United States Patent [19]

Carr

[11] Patent Number: 5,782,897
[45] Date of Patent: Jul. 21, 1998

[54] MICROWAVE HEATING APPARATUS FOR RAPID TISSUE FIXATION

[75] Inventor: Kenneth L. Carr, Harvard, Mass.

[73] Assignee: Microwave Medical Systems, Inc., Littleton, Mass.

[21] Appl. No.: 586,399

[22] Filed: Jan. 16, 1996

Related U.S. Application Data

[63] Continuation-in-part of Ser. No. 380,815, Jan. 30, 1995, which is a continuation of Ser. No. 124,928, Sep. 21, 1993, abandoned, which is a continuation of Ser. No. 808,854, Dec. 16, 1991, abandoned, which is a continuation of Ser. No. 67,626, Jun. 26, 1987, Pat. No. 5,073,167.

[51] Int. Cl.$^6$ ............................................. A61B 17/36
[52] U.S. Cl. ........................ 607/101; 607/103; 607/96; 606/27; 606/33
[58] Field of Search ................. 607/96–104; 606/27–33

[56] References Cited

U.S. PATENT DOCUMENTS 4,715,727 12/1987 Carr ............................................. 128/736
4,891,239 1/1990 Dudley ........................................ 219/683

*Primary Examiner*—David M. Shay
*Attorney, Agent, or Firm*—Cesari and McKenna, LLP

[57] ABSTRACT

Microwave heating apparatus for fixating tissue comprises an electrically conductive waveguide structure having opposite first and second walls each of which has opposite first and second ends and a longitudinal centerline. A body of non-magnetic dielectric material inside the waveguide structure bridges the first and second walls preferably at their centerlines. A pocket extends through a wall of the waveguide structure into the body and a tissue holder containing contents, namely a tissue sample and a fixation solution, is arranged to be received in the pocket. The dielectric constant of the body is selected to closely match the composite dielectric constant of the tissue holder and its contents so that when microwave power is delivered into the waveguide structure for heating a succession of samples, variations in the dielectric properties of the different samples will not significantly affect the tuning of the waveguide structure. A radiometric sensor may be coupled to the waveguide structure so that the temperature of the tissue sample may be monitored non-invasively for temperature control and display purposes.

16 Claims, 2 Drawing Sheets

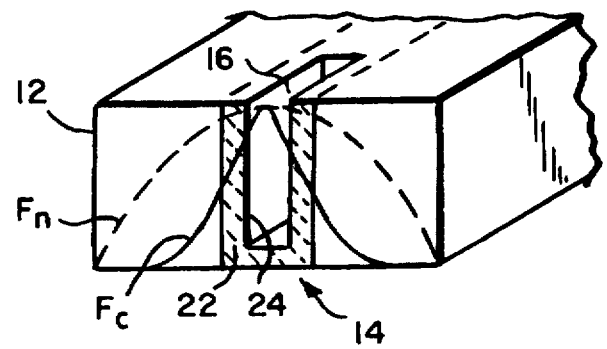
FIG. 3
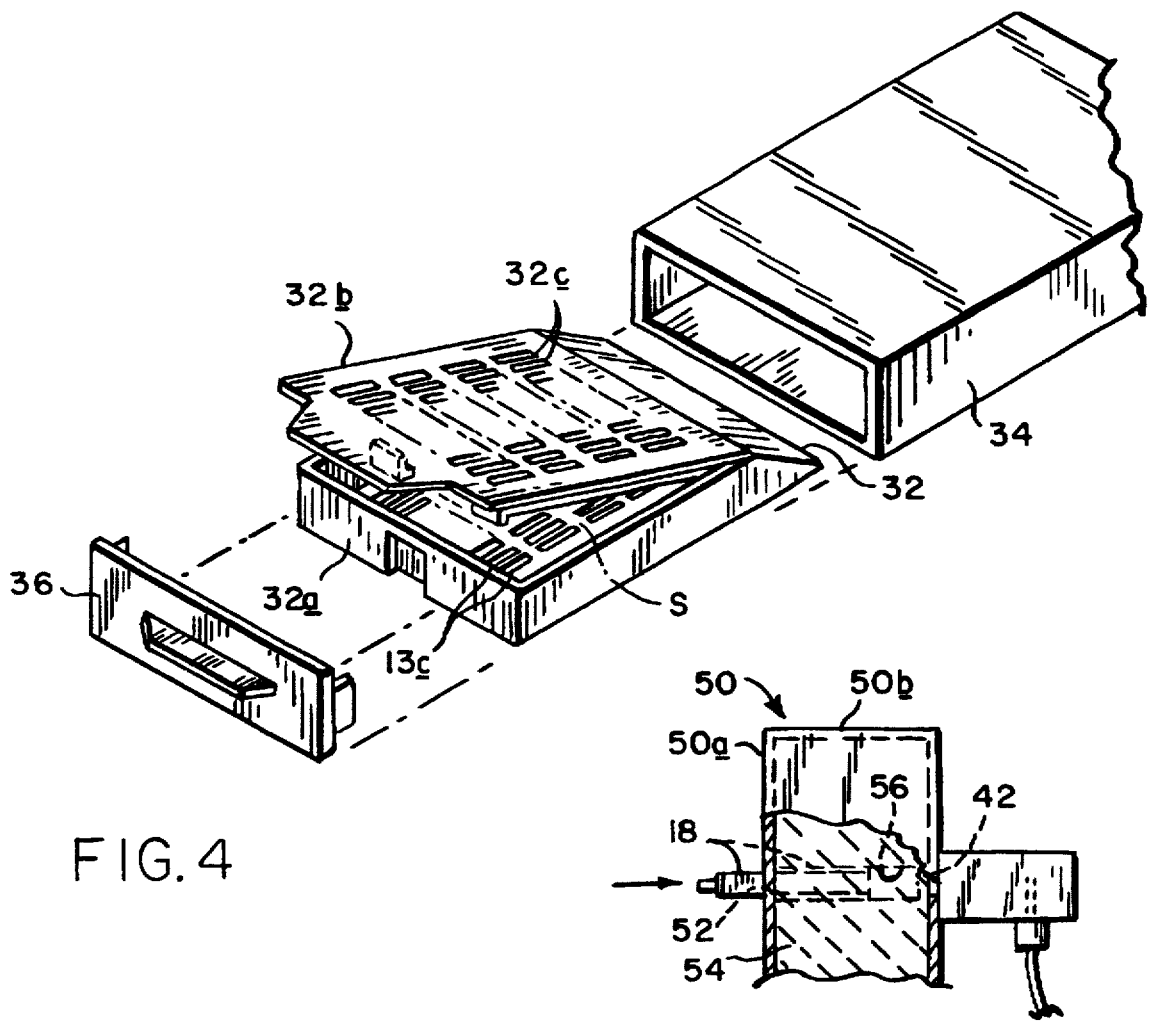
FIG. 4
FIG. 5

MICROWAVE HEATING APPARATUS FOR RAPID TISSUE FIXATION

RELATED APPLICATIONS

This application is a continuation-in-part of Ser. No. 08/380.815, filed Sep. 6, 1994, which is a continuation of Ser. No. 08/124,928, filed Sep. 21, 1993, now abandoned, which is a continuation of Ser. No. 07/808,854, filed Dec. 16, 1991, now abandoned, which is a continuation of Ser. No. 07/067,626, filed Jun. 26, 1987, now U.S. Pat. No. 5,073,167.

FIELD OF THE INVENTION

This invention relates to apparatus for fixating biopsy tissues for histopathologic examination. It relates especially to microwave heating apparatus which accelerates the rate at which a chemical preserving solution penetrates the walls of tissue cells to achieve rapid tissue fixation.

BACKGROUND OF THE INVENTION

Diseases are often diagnosed by examining tissue samples from biopsies. Obviously, it is important that the tissue cells be examined as close as possible to the living state. Accordingly, they are usually put through a chemical fixation process in order to stop or slow down cell degradation. Historically, the samples were immersed for hours in an aldehyde-containing preserving solution during which time penetration and cross-linking of the protein components of the tissue occurred thereby greatly retarding subsequent cell degradation. Following fixation, a pathologist would then subject the samples to various tests and examinations to reach a diagnosis.

Of late, faster data acquisition and a shorter turnaround time from the pathology laboratory have become increasingly important in order to provide the best possible diagnostic services. Computers have made possible the faster reporting of laboratory data. Automated tissue processors and stainers have improved sample flow through the laboratory. However, until recently, there have been no significant improvements in tissue fixation. Resultantly, tissue fixation has been the bottleneck between receipt of a sample in the pathology laboratory and the subsequent automated histology processing of the tissue because all such processing must wait until tissue fixation is complete.

In recent years, microwave energy has been used to speed up the rate at which the preserving solution penetrates the cell walls during fixation. Time-saving microwave fixation technology offers the opportunity to study biopsy samples with less exposure to aldahydes and it also eliminates many of the artifacts associated with prolonged fixation. Indeed, it has been shown that microwave radiation used in conjunction with low concentrations of aldahyde is capable of fixing standard biopsy-size samples in a matter of seconds. This is important not only because it saves processing time, but also because the tissue cells have less time to degrade and therefore the quality of the fixated tissue is enhanced.

Tissue fixation by microwave heating was originally accomplished using a standard microwave oven or variants thereof; see, for example, U.S. Pat. No. 5,068,086. The early microwave heating apparatus are disadvantaged because they heat the sample in a non-uniform manner so that some areas of the tissue may become overheated and be destroyed, while other areas may not become fixated at all. The use of a carrousel to move the sample within the microwave field alleviates this problem to some extent, but makes it more difficult to position the samples and to automate the fixation process. Also, a microwave oven operates inconsistently because its fields constantly change throughout the oven. These changes cause different heat patterns within the sample each time the sample is fixated. Such inconsistency can cause errors in analysis. Venting of the fumes produced by the fixation solution is also a problem. Finally, microwave oven-type heaters are disadvantaged because they invariably rely on probes which project into the heating cavity or even into the sample itself thereby producing additional non-uniformities and artifacts in the microwave heating field.

To avoid the above problems, there has been developed recently a microwave heater for tissue fixation in the form of a single mode resonant waveguide section with an aperture near one end. Tissue is placed into a container filled with a small volume of fixation solution. The container and tissue are then inserted through the aperture into the waveguide. Microwave energy is coupled into the waveguide section and applied to the tissue which becomes fixated within a second or less. Such heating apparatus is described in detail in U.S. Pat. No. 4,891,239.

While that patented microwave heating apparatus is an improvement over the microwave oven-type heaters, its use is complicated by the fact that it has to be tuned each time a sample is to be fixated because the different dielectric properties of the biological samples cause changes in the resonant frequency of the waveguide. In that patented device, such tuning is accomplished by adjusting the position in the waveguide of the vial that contains the sample.

Another disadvantage of that patented apparatus is that a relatively wide aperture must be provided in the waveguide in order to receive the sample-holding vial. To prevent the escape of microwave energy from the waveguide through that aperture, a special choke and metal cover are required at that aperture. Such requirements for tuning and shielding increase the cost and complexity of the apparatus and make it more difficult to adapt it to automated operation.

In addition, like the above described microwave ovens, that patented waveguide-type heater monitors the temperature of the sample with a temperature probe that projects into the waveguide and may produce artifacts in the field pattern therein. For these and other reasons, up to now, the use of waveguide resonators as microwave heaters for rapid tissue fixation has not been as widespread as one might expect considering their distinct advantages in terms of speed and reproducibility of results.

SUMMARY OF THE INVENTION

Accordingly, the present invention aims to provide a reliable microwave heating apparatus for achieving fast, uniform tissue fixation.

Another object of the invention is to provide such heating apparatus which can decrease the handling time of tissue biopsies.

A further object of the invention is to provide heating apparatus of this type which is easily adapted to automated operation so as to be able to heat a succession of different tissue samples.

Yet another object of the invention is to provide microwave heating apparatus for tissue fixation which does not require retuning before each fixation cycle.

Still another object of the invention is to provide such microwave heating apparatus which does not require any special choke structure or shielding to prevent radiation leakage from the apparatus.

A further object of the invention is to provide apparatus of this type which can monitor fixation temperature continuously and non-invasively.

Other objects will, in part, be obvious and will, in part, appear hereinafter. The invention accordingly comprises the features of construction, combination of elements and arrangement of parts which will be exemplified in the following detailed description, and the scope of the invention will be indicated in the claims.

Briefly, the heating apparatus of this invention comprises a rectangular waveguide cavity resonator. Unlike a microwave oven, it is a tuned, single mode microwave structure designed to provide a uniform deposition of power to a tissue sample. The waveguide structure has opposite first and second elongated walls each of which has opposite first and second ends and a longitudinal centerline. A body of non-magnetic dielectric material is disposed inside the waveguide structure so as to bridge the first and second walls, preferably at their centerlines. The apparatus also includes a pocket which extends through the first wall of the waveguide structure into the dielectric body. This pocket may form a non-radiating slot in the waveguide structure and is sized to receive a tissue holder containing a tissue sample and a fixating solution. In accordance with the invention, the dielectric constant of the dielectric body is chosen to closely match composite dielectric constant of the holder and its contents. In this way, the tissue sample will only represent a small portion of the total dielectric loading in the waveguide structure. Resultantly, variations in the dielectric properties of different tissue samples will not significantly affect the tuning of the waveguide structure so that the apparatus does not have to be retuned when fixating a succession of tissue samples. Moreover, since, as noted above, the tissue samples may be loaded into the apparatus via a non-radiating slot, radiation shielding may not be required at that location. Both of the above factors facilitate the automatic fixation of a large number of samples by the apparatus.

BRIEF DESCRIPTION OF THE DRAWINGS

For a fuller understanding of the nature and objects of the invention, reference should be had to the following detailed description, taken in connection with the accompanying drawings, in which:

FIG. 3 is a diagrammatic view illustrating the operation of the FIG. 1 apparatus;

FIG. 4 is an exploded perspective view on a larger scale showing a sample holder for use in the FIG. 1 apparatus, and FIG. 5 is a fragmentary plan view with parts broken away showing a second apparatus embodiment.

DESCRIPTION OF THE PREFERRED EMBODIMENTS

Figure 1:
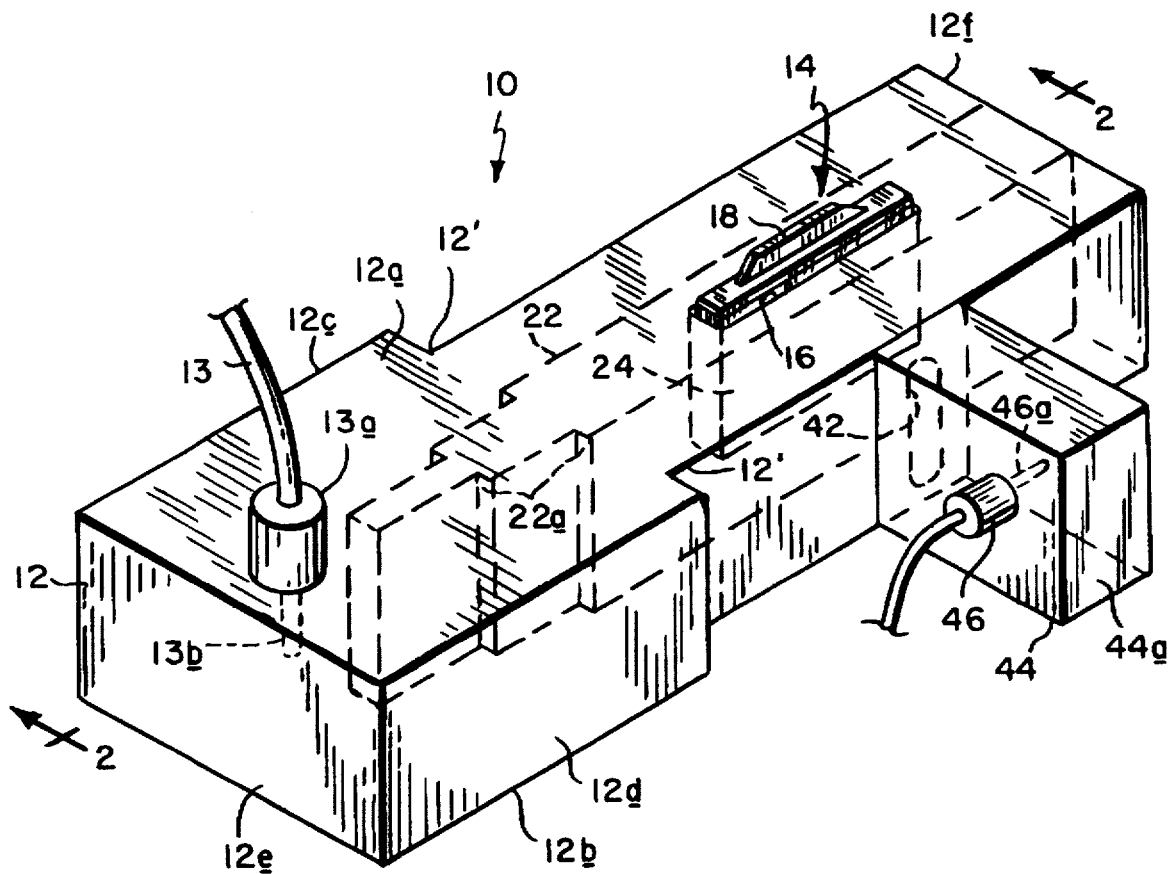
FIG. 1 is an perspective view of microwave heating apparatus for rapid tissue fixation according to the invention.
Figure 2:
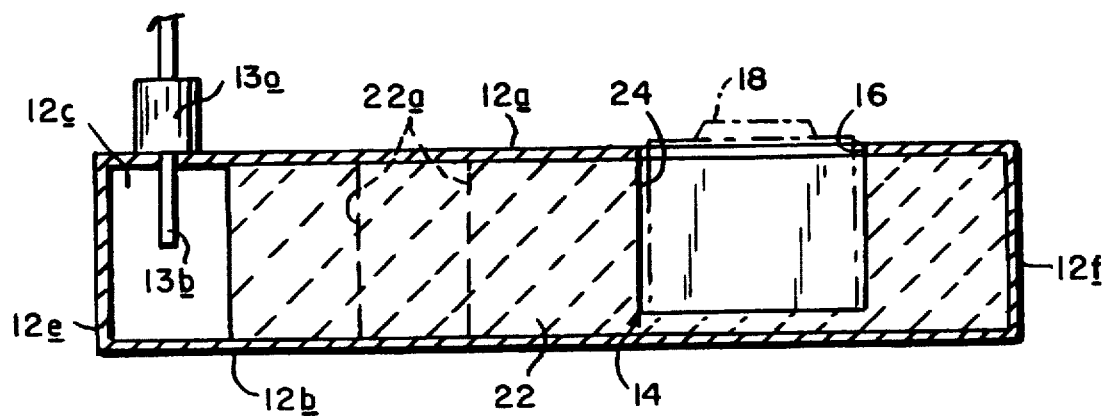
FIG. 2 is a sectional view taken along line 2—2 of FIG. 1.

The heating apparatus, shown generally at 10, comprises a generally rectangular waveguide cavity resonator 12 having relatively broad top and bottom walls 12a and 12b, a pair of opposite narrower side walls 12c and 12d and a pair of opposite end walls 12e and 12f. The resonator receives power ($TE_{10}$) from a conventional microwave source (not shown) by way of a coaxial cable 13 which may be terminated by a standard Type N connector 13a and an associated probe 13b mounted to a broad wall, e.g., wall 12a, of resonator 12, ¼ wavelength from its end 12e. A suitable controllable microwave source is described in U.S. Pat. No. 5,073,167, the contents of which are hereby incorporated by reference herein.

The waveguide resonator 12 is sized to optimize propagation of microwave energy at the frequency selected for the microwave source. For example, for a microwave source which operates at a frequency of 2.45 GHz, the resonator may be the equivalent of standard WR-340 waveguide which has a width of 3.40 inch and a height of 1.70 inch. These dimensions place the frequency of operation of the resonator in an ideal location with respect to the operating band of the resonator. It is sufficiently far enough away from the cut-off frequency, i.e. 1.735 MGz, such that minimum attenuation is obtained for the $TE_{10}$ mode of propagation; yet higher order modes are cut-off.

Thus, the resonator 12 is basically a rectangular waveguide section shorted at both ends. It is resonant at frequencies where its length is a multiple of half-wavelengths so that the transverse electric field is zero at the opposite ends of the resonator. If the resonator is two half wavelengths long, the transverse field will be a maximum at ¼ wavelength from each end of the resonator. Locating a tissue sample S (FIG. 4) at the point of maximum field strength will place the sample at the region of maximum power absorption or heating, herein referred to as the heating region 14.

In order to access heating region 14, an aperture 16 is provided in a broad wall 12a of the resonator. Aperture 16 is in the form of a narrow slot which is aligned with and located on the longitudinal centerline of the resonator wall 12a, the transverse centerline of the aperture 16 being ¼ wavelength from the end wall 12f of the resonator. Typically, aperture 16 is in the order of 3.6 cm long and 1 cm wide.

Due to its placement and dimensions, aperture 16 is a so-called non-radiating slot. More particularly, radiation or coupling from a waveguide through an aperture in the waveguide wall is due to both electric and magnetic coupling. For the case of a narrow slot such as aperture 16, the coupling is essentially magnetic. Only the magnetic field component parallel to the long dimension of the slot aperture couples through the aperture. On the other hand, if slot 16 were wider or displaced laterally away from the longitudinal centerline of the resonator, it would become a radiating slot.

An alternative way of viewing magnetic coupling is in terms of interruption of conduction currents, both longitudinal and transverse. A narrow aperture 16 on the centerline of the radiator is non-radiating since it does not interrupt any conduction currents. On the other hand, if aperture 16 were wider or rotated 90°, it would interrupt the longitudinal conduction currents and therefore become a radiating aperture.

For a description of the electric and magnetic fields and conduction currents in a rectangular waveguide, see Principles and Applications of Waveguide Transmission by George C. Southworth, BTL; D Van Nostrand Co., Inc. N.Y. 1950, page 3, the contents of which is hereby incorporated by reference herein.

The aperture 16 permits insertion of a sample holder 18 containing a tissue sample S into the heating region 14. Maximum attenuation per length is achieved by having the tissue sample parallel to the electric field and at the center of the resonator as shown where the $TE_{10}$ electric field is maximum. Attenuation is a function of frequency, generally increasing with increasing frequency. Since the aperture 16 is a non-radiating slot, no cover or choke structure need be provided at the aperture where it would be in position to complicate the insertion and removal of the holder 18.

The sample holder 18 is not simply presented to the heating region 14 through aperture 16. Rather, it is positively supported there by a slab 22 of a non-magnetic dielectric material such as aluminum oxide ceramic. Slab 22 is placed across the narrow dimension, i.e., height, of the resonator at the centerline of the resonator. Preferably, the slab extends from the resonator end wall 12f past the heating region 14 near to the opposite end wall 12e. Slab 22 is somewhat wider than aperture 16 in the heating region 14. But further along toward the end 12e of the resonator, slab 22 may be narrowed continuously or in steps as shown at 22a to provide a gradual transition from probe 13a into the dielectric-loaded end of the resonator 12 so as to minimize energy reflections in the resonator.

The dielectric slab 22 has several different functions in apparatus 10. First, as just stated, it is used to position and support the sample holder 18 in heating region 14. For this, the slab is provided with a vertical recess 24 in register with aperture 16, the aperture and recess forming a pocket sized to snugly, but slidably, receive the sample holder 18.

Secondly, the dielectric slab 22 creates a capacitively-loaded waveguide segment within the resonator 12. The introduction of such E-plane dielectric loading alters the field distribution within resonator 12 so as to concentrate the microwave field pattern toward the sample holder 18 by virtue of the dielectric properties of the structure. This is illustrated in FIG. 3 which is a diagrammatic view of the interior of resonator 12 at the heating region 14. Without the presence of the dielectric slab 22, there would be a normal field distribution represented by the waveform $F_n$ in that figure. With dielectric loading, the field distribution is more concentrated, as shown by the solid line curve $F_c$. Thus, slab 22 localizes the field at the heating region 14 which contains the sample holder 18.

The dielectric loading of resonator 12 by slab 22 does decrease the resonator cut-off frequency to some extent. To compensate for this, the width of the dielectric-loaded end of the resonator 12 may be reduced. In other words, the resonator side walls 12c and 12d adjacent slab 22 may be stepped toward one another as shown at 12' in FIG. 1.

The dielectric slab 22 performs a third important function in apparatus 10. More particularly, the slab is used to effectively broaden the bandwidth of the resonator so as to enable the resonator to heat a variety of biological samples without retuning. More particularly, It has been found that the introduction of the tissue sample S will not alter the field distribution within resonator 12 if the relative dielectric constant of the tissue sample is similar to that of the slab 22. The slab, having a very low loss tangent, is virtually lossless at microwave frequencies. The tissue, on the other hand, is very absorptive so that in the sample, the microwave energy is converted to heat. In accordance with the invention, then, the dielectric constant of the E-plane dielectric slab 22 is chosen to closely match the dielectric properties of the loaded sample holder 18, i.e., the holder plus sample S and the fixating solution. The tissue sample S will represent but a small portion of the total dielectric loading in the waveguide structure. As a result, variations in the dielectric properties of different samples S will not significantly alter the tuning of the resonator 12. Therefore, it is not necessary to retune the resonator when fixating a succession of samples. This is a definite advantage in that it facilitates automating apparatus 10 to process large numbers of samples.

Refer now to FIG. 4 which shows the sample holder 18 in greater detail. The holder 18 includes a standard tissue cassette 32 which is a rectangular plastic container about 3 cm×2.5 cm×0.3 cm, consisting of a box-like base 32a and a cover 32b both of which have numerous slits 32c on their broad surfaces. Cassette 32 has a holding volume of about 2.3 cm³ for containing a tissue sample S whose volume is about 1 cm³. The remaining volume of cassette 32 is filled with a fixating liquid such as an aldehyde-containing solution, a buffered solution, a polyethylene glycol solution, or the like. The tissue cassette is, in turn, normally placed in a small, thin-walled impervious plastic box or cuvette 34 having a cover 36. The box and cover retain the solution in the holder during the fixation process. The plastic of both the cassette 32 and the cuvette 34, 36 has a relative dielectric constant of, say, 2.5 and a low loss tangent of approximately 0.001. The composite dielectric constant and loss tangent of the plastic, fixation solution and tissue sample S may be determined by measurement of both the attenuation and return loss in resonator 12. There is virtually no attenuation due to the plastic. Therefore, substantially all power absorption will occur in the tissue sample S and the fixating solution.

Referring again to FIG. 1, the fixation apparatus 10 of this invention measures the temperature of the sample S in holder 18 non-invasively using radiometric sensing. For this, a narrow, vertical slot 42 is provided in a resonator side wall, e.g., wall 12d, directly opposite the heating region 14. Slot 42 is dimensioned and oriented so that it is a non-radiating slot (as explained above) at the relatively low heating frequency. Slot 42 opens into a receiving waveguide 44 mounted to side wall 12d. Waveguide 44 is a rectangular structure whose broad dimension or width is less than the narrow dimension or height of the resonator 12. This forms a dual-mode transducer capable of operating at both the heating frequency of 2.45 GHz and the radiometric or received frequency of about 4 GHz, as described in Applicant's above '167 patent. This dual-mode arrangement wherein the smaller receive waveguide 44 is orthogonal to resonator 12 and coupled thereto through the slot 42 has two important advantages. First, the resonator 12 will serve as a horn, increasing the size of the aperture of the receiving waveguide 44; that is, the height of the resonator is greater than the width of waveguide 44. The orthogonality of the two waveguides 12 and 44 provides added isolation between the transmit and receive functions of apparatus 10. Finally, the smaller waveguide 44 acts as a high-pass filter adding significant attenuation at the heating frequency and providing isolation between the transmitter and the sensitive radiometer associated with the receiving waveguide 44.

During operation of apparatus, the sample S at heating region 14 will absorb power and become heated. As the temperature of the sample increases, the density of the radiation at all frequencies increases and an appreciable amount of this radiation exists in the microwave segment of the frequency spectrum. This energy is coupled into the receiving waveguide 44 and is detected by the probe 46' of a waveguide-to-coaxial connector 46 mounted to a sidewall of waveguide 44 adjacent to the end wall 44a thereof. Connector 46 is preferably spaced from wall 44a ¼ wavelength at the detected frequency. Connector 46 couples a signal representing the temperature of the sample S in holder 18 to a standard radiometer (not shown) which produces an output signal indicative of that temperature. A suitable radiometer is available from Microwave Medical Systems, Inc., Acton, Mass. Its output signal may be used to control the power of the microwave source, as described in my '167 patent, to bring the sample to a selected final fixation temperature and to display that temperature on an associated display (not shown).

As stated above, the receiving waveguide 44 preferably operates at a frequency which is much higher than that of the microwave source. For example, in the illustrated apparatus 10, the waveguide 44 may operate at 4.7 GHz which is about twice the heating frequency. By this manner of frequency selection, the heating frequency is highly attenuated in the waveguide 44, thereby providing protection for the sensitive microwave radiometer associated with that waveguide and assuring that the signal that is detected is truly representative of the temperature of the sample S in the heating region 14.

When fixating samples S, a holder 18 containing a tissue sample may be deposited manually or automatically through aperture 16 into recess 24. Then, the microwave source associated with apparatus 10 may be activated for a brief period, i.e., less than 1 second, to produce a strong field at the heating region 14 of resonator 12. Since the slab 22 has a very low loss tangent, it is virtually lossless at microwave frequencies. Therefore, substantially all of the microwave energy is used to heat the tissue sample S which is very absorptive. The temperature of the tissue sample is continuously sensed radiometrically by waveguide 44 and the associated radiometer, with the output of the radiometer being used to control the transmitter to prevent underheating or overheating of the sample.

When a particular sample has been fixated, a controller associated with the apparatus 10 may control a conventional automatic feeder (not shown) to remove the sample holder 18 from aperture 16 and to insert a succeeding holder containing a different sample. Thus, the apparatus 10 facilitates the automatic sequencing of tissue samples for fixation. Since the apparatus can process tissue samples in less than a second, it is not even necessary to turn off the associated transmitter between samples and, due to the presence of the dielectric slab 22, it is not necessary to tune resonator 12 from one sample to the next. Nor is it required to provide a special choke or cover for the sample-receiving aperture 16 because that aperture may be designed as a non-radiating slot which does not allow energy to escape from the resonator.

Refer now to FIG. 5 which shows a somewhat different resonator 50 which has a non-radiating aperture 52 in a narrow wall 50a of the resonator for accepting a sample holder 18 so that the sample holder can extend into the resonator perpendicular to the longitudinal centerline of the resonator. Preferably, the longitudinal centerline of slot 52 is positioned ¼ wavelength from the adjacent end wall 50b of the resonator.

Positioned inside resonator 50 is a dielectric slab 54 containing a recess 56 in register with aperature 52.

As with apparatus 10 described above, a sample holder 18 inserted into the recess 56 is supported by the slab at a position of maximum energy or heating within the resonator. Preferably, the slab 54 is wider than the sample holder 18, at least in the vicinity of slot 52, so that it can receive and support the holder 18 and carry out the other functions described above in connection with slab 22 in FIG. 1. In this embodiment, the wider slab 54 produces an energy distribution within the waveguide structures which has a rather flat waveform Fc (FIG. 3) across the width of the slab so that there is a uniform heating pattern across the width of the tissue sample.

It is, of course, also feasible to orient the top loading aperture 16 and recess 24 of the FIG. 1 apparatus 90° from the position shown in that figure so that the sample holder 18 is positioned orthogonal to the longitudinal centerline of the resonator 12. The disadvantage with that design is that the aperture 52 is no longer a non-radiating slot. However, that problem may be overcome by providing a movable length of rectangular waveguide (not shown), similar to waveguide 44, over the aperture. The cross-section of that waveguide should be small enough to prevent wave propagation through aperture 52 thereby creating a cut-off waveguide or high pass filter. That waveguide may be hinged or slidably connected to the resonator top wall 12a so that it can be moved away from aperture 16.

It will thus be seen that the objects set forth above, among those made apparent from the preceding description, are efficiently attained. Also, since certain changes may be made in the above construction without departing from the scope of the invention, it is intended that all matter contained in the above description or shown in the accompanying drawings be interpreted as illustrative and not in a limiting sense.

It is also to be understood that the following claims are intended to cover all of the generic and specific features of the invention described herein.

What is claimed is:

1. Microwave heating apparatus for fixating tissue, said apparatus comprising
   an electrically conductive waveguide structure having opposite first and second walls each having a longitudinal centerline;
   source means for producing conduction currents in said waveguide structure;
   a body of non-magnetic dielectric material inside said waveguide structure and which bridges said first and second walls at said centerline;
   a pocket extending through a wall of said waveguide structure into said body and for receiving a tissue holder, said pocket having an entrance in the form of a narrow slot in a wall of the waveguide structure which does not appreciably interrupt conduction currents produced in the waveguide structure by the source means, and
   a tissue holder in said pocket, said tissue holder containing contents namely a tissue sample and a fixation solution, said holder and contents having a composite dielectric constant which closely matches the dielectric constant of said body.

2. The apparatus defined in claim 1 wherein said slot extends along the longitudinal centerline of said first wall.

3. The apparatus defined in claim 1 wherein said slot extends perpendicular to the longitudinal centerline of said first wall.

4. The apparatus defined in claim 3 wherein said slot is located in said first wall.

5. The apparatus defined in claim 3 wherein said slot is located in a wall of said waveguide structure that extends between said first and second walls.

6. Microwave heating apparatus for fixating tissue contained in a tissue holder, said apparatus comprising
   an electrically conductive waveguide structure having
      opposite first and second walls each of which has opposite first and second ends and a longitudinal centerline, and
      opposite third and fourth walls connecting said first and second walls;
   a body of non-magnetic dielectric material inside said waveguide structure and which extends between said first and second walls at said centerlines;

a pocket extending through a wall of said waveguide structure into said body and for receiving said tissue holder;

source means for delivering microwave power into said waveguide structure for heating said sample when the tissue holder is received in said pocket, and a tissue holder containing contents namely a tissue sample and a fixation solution, said holder and contents having a composite dielectric constant and arranged to be received in said pocket, the dielectric constant of said body being closely matched to said composite dielectric constant.

7. The apparatus defined in claim 6 wherein said body comprises an elongated slab whose width is substantially less than that of said waveguide structure and which extends from the first ends of said first and second walls along said centerlines toward the second ends thereof, and said source means comprise a probe projecting into said waveguide structure through one of said first and second walls substantially at the longitudinal centerline thereof and between the second end of said one of said walls and said slab.

8. The apparatus defined in claim 6 wherein the width of said body decreases between said pocket and said wall second ends.

9. The apparatus defined in claim 6 wherein said body is of aluminum oxide.

10. The apparatus defined in claim 6 and further including temperature monitoring means mounted to said waveguide structure substantially opposite said pocket for monitoring the temperature of said sample.

11. The apparatus defined in claim 10 wherein said temperature monitoring means comprise radiometric detection means coupled to the interior of said waveguide structure and which monitors the sample temperature non-invasively.

12. The apparatus defined in claim 6 wherein said pocket has an entrance comprising a narrow non-radiating slot in a wall of the waveguide structure.

13. The apparatus defined in claim 12 wherein said slot extends along the centerline of said first wall.

14. The apparatus defined in claim 12 wherein said slot is located in said third wall and extends perpendicular to said centerlines of said first and second walls, and said body is wider than the depth of said pocket.

15. The apparatus defined in claim 6 wherein said holder is of a plastic material which is substantially transparent to microwave energy at the frequency of said source.

16. The apparatus defined in claim 15 wherein said holder comprises a fluid-tight box-like enclosure, and a cassette for holding said tissue sample, said cassette having openings therein and being shaped and dimensioned for containment within said enclosure.

\* \* \* \* \*